(12) United States Patent
Helmer et al.

(10) Patent No.: US 11,197,963 B2
(45) Date of Patent: Dec. 14, 2021

(54) DEVICE FOR ATTACHMENT TO AN INJECTION DEVICE

(71) Applicant: SANOFI-AVENTIS DEUTSCHLAND GMBH, Frankfurt am Main (DE)

(72) Inventors: Michael Helmer, Frankfurt am Main (DE); Stefan Wendland, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 752 days.

(21) Appl. No.: 15/761,731

(22) PCT Filed: Sep. 20, 2016

(86) PCT No.: PCT/EP2016/072333
§ 371 (c)(1),
(2) Date: Mar. 20, 2018

(87) PCT Pub. No.: WO2017/050781
PCT Pub. Date: Mar. 30, 2017

(65) Prior Publication Data
US 2018/0353699 A1    Dec. 13, 2018

(30) Foreign Application Priority Data
Sep. 23, 2015    (EP) .................................... 15186460

(51) Int. Cl.
*A61M 5/315*    (2006.01)
*A61M 5/20*    (2006.01)
(Continued)

(52) U.S. Cl.
CPC .......... *A61M 5/31568* (2013.01); *A61M 5/20* (2013.01); *A61M 5/24* (2013.01);
(Continued)

(58) Field of Classification Search
CPC .. A61M 5/31568; A61M 5/20; A61M 5/3213; A61M 2005/3126;
(Continued)

(56) References Cited

U.S. PATENT DOCUMENTS

| 2010/0145656 A1 | 6/2010 | Koehler et al. | |
| 2011/0313349 A1* | 12/2011 | Krulevitch | A61M 5/315 604/65 |

(Continued)

FOREIGN PATENT DOCUMENTS

| CN | 101727540 | 6/2010 |
| CN | 102369029 | 3/2012 |

(Continued)

OTHER PUBLICATIONS

International Search Report and Written Opinion in International Application No. PCT/EP2016/072333, dated Jan. 19, 2017, 10 pages.

(Continued)

*Primary Examiner* — Amber R Stiles
*Assistant Examiner* — Alexandra Lalonde
(74) *Attorney, Agent, or Firm* — Fish & Richardson P.C.

(57) ABSTRACT

A supplementary device is configured to be attached to a drug delivery device. The supplementary device comprises a non-contact sensor configured to output signals indicative of the position of a moveable component within the drug delivery device. The supplementary device further comprises a processor configured to receive the signals output from the non-contact sensor. This processor is additionally configured to determine, based on the signals, whether the drug delivery device is in a pre-activation state or a post-activation state.

14 Claims, 7 Drawing Sheets

(51) Int. Cl.
   *A61M 5/32* (2006.01)
   *G16H 20/17* (2018.01)
   *A61M 5/24* (2006.01)
   *A61M 5/50* (2006.01)
   *A61M 5/31* (2006.01)

(52) U.S. Cl.
   CPC ........ *A61M 5/3213* (2013.01); *A61M 5/5086* (2013.01); *G16H 20/17* (2018.01); *A61M 2005/3126* (2013.01); *A61M 2005/3142* (2013.01); *A61M 2205/3317* (2013.01); *A61M 2205/3561* (2013.01); *A61M 2205/3569* (2013.01); *A61M 2205/3584* (2013.01); *A61M 2205/505* (2013.01); *A61M 2205/52* (2013.01); *A61M 2205/583* (2013.01); *A61M 2205/6063* (2013.01); *A61M 2205/6081* (2013.01); *A61M 2205/8206* (2013.01)

(58) Field of Classification Search
   CPC .. A61M 2005/3142; A61M 2205/3317; A61M 2205/52; A61M 2205/3592; G06F 19/3468; G16H 20/17
   See application file for complete search history.

(56) References Cited

U.S. PATENT DOCUMENTS

| | | | | |
|---|---|---|---|---|
| 2014/0243750 | A1* | 8/2014 | Larsen | A61M 5/1452 604/189 |
| 2015/0268656 | A1 | 9/2015 | Bammer et al. | |
| 2016/0015910 | A1* | 1/2016 | Mukai | A61M 5/50 206/365 |

FOREIGN PATENT DOCUMENTS

| | | |
|---|---|---|
| CN | 102725011 | 10/2012 |
| CN | 103648552 | 3/2014 |
| CN | 103957961 | 7/2014 |
| CN | 104519931 | 4/2015 |
| CN | 104888316 | 9/2015 |
| EP | 1095668 | 5/2001 |
| EP | 2182456 | 5/2010 |
| JP | 2012-519025 | 8/2012 |
| JP | 2014-531283 | 11/2014 |
| JP | 2015-532136 | 11/2015 |
| WO | WO 2010/089304 | 8/2010 |
| WO | WO 2010/098927 | 9/2010 |
| WO | WO 2011/089205 | 7/2011 |
| WO | WO 2012/046199 | 4/2012 |
| WO | WO 2013/010893 | 1/2013 |
| WO | WO 2013/050535 | 4/2013 |
| WO | WO 2014/023763 | 2/2014 |
| WO | WO 2015/138093 | 9/2015 |

OTHER PUBLICATIONS

International Preliminary Report on Patentability in International Application No. PCT/EP2016/072333, dated Mar. 27, 2018, 7 pages.

* cited by examiner

DEVICE FOR ATTACHMENT TO AN INJECTION DEVICE

CROSS REFERENCE TO RELATED APPLICATIONS

The present application is the national stage entry of International Patent Application No. PCT/EP2016/072333, filed on Sep. 20, 2016, and claims priority to Application No. EP 15186460.0, filed in on Sep. 23, 2015, the disclosures of which are expressly incorporated herein in entirety by reference thereto.

TECHNICAL FIELD

The present disclosure relates to a device configured to retain an injection device or syringe and to remind a user when a medicament injection is due.

BACKGROUND

A variety of diseases exists that require regular treatment by injection of a medicament. Such injection can be performed by using injection devices, which are applied either by medical personnel or by patients themselves.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages for the user from this approach. If the user stops pressing the button/plunger, then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus, it can be inconvenient for the user to reach a fully extended button. The combination of injection force and button extension can cause trembling/shaking of the hand, which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, allergies, hormone therapies, anticoagulants etc. Auto-injector devices can be used to deliver a single dose of a particular life-saving drug. For example, they are often prescribed to people who are at risk for anaphylaxis. They are also often used in the military to protect personnel from chemical warfare agents. Alternatively, auto-injectors are used to administer medicaments according to a prescribed therapeutic schedule for people suffering from Multiple Sclerosis, Rheumatroid Arthritis, Anemia, e.g.

Auto-injectors may be disposable or single use devices which may only be used to deliver one dose of medicament and which have to be disposed of after use. Other types of auto-injectors may be reusable. Usually they are arranged to allow a user to load and unload a standard syringe. The reusable auto-injector may be used to perform multiple parenteral drug deliveries, whereas the syringe is disposed after having been spent and unloaded from the auto-injector. The syringe may be packaged with additional parts to provide additional functionality.

In a typical scenario disease can be treated by patients themselves by injection of medicament doses using an auto-injector, for example on a daily, weekly, bi-weekly, or monthly basis.

SUMMARY

A first aspect provides a supplementary device configured to be attached to a drug delivery device, the supplementary device comprising a non-contact sensor configured to output signals indicative of the position of a moveable component within the drug delivery device; and a processor configured to receive the signals output from the non-contact sensor and to determine based on the signals whether the drug delivery device is in a pre-activation state or a post-activation state.

This allows the supplementary device to notify a user regarding the operational state of the device and the supplementary device may do this more clearly and effectively than the drug delivery device. Using a non-contact sensor allows the supplementary device to monitor the drug delivery device without any increase in friction on the mechanical components of the drug delivery device. The moveable component within the drug delivery device is already present in the design of the mechanism of the drug delivery device and therefore no significant modifications to the way in which this mechanism operates are required. Thus, the increases in the complexity of manufacture of the drug delivery device are minor.

The non-contact sensor may be a capacitive sensor. Components of the capacitive sensor may be arranged within the supplementary device such that the attached drug delivery device forms at least a part of a dielectric layer of the capacitive sensor. The capacitive sensor may comprise opposing sets of at least one electrically conductive plate.

The non-contact sensor may be a Hall sensor configured to measure a magnetic field produced by the moveable component within the drug delivery device.

Upon determining that the drug delivery device has changed from a pre-activation state to a post-activation state, the processor may be configured to cause an indication to be output which informs a user regarding a dwell time of the drug delivery device. The supplementary device may further comprise a display unit. Causing an indication to be output may comprises causing one or more graphical elements to be displayed on the display unit, the graphical elements communicating a progress of the dwell time.

This is advantageous as it assists the user in using the drug delivery device correctly and in particular reduces the risk of the user performing an underdose by removing the needle of the drug delivery device too soon after injection of the medicament.

The supplementary device may further comprise at least one memory. The processor may be configured to cause information relating to a last performed injection operation to be stored in the memory upon determining that the drug delivery device has changed from a pre-activation state to a post-activation state. The information may comprise at least a time stamp associated with the last performed injection operation. The information may further comprise a medicament dose amount and/or a medicament type.

Storing this information electronically allows it to be communicated easily to other devices and people, such as the user's doctor. It also allows the user to have greater oversight and control of their medication regime.

The processor may have access to or may be configured to calculate a time of next injection and may be further configured to produce a reminder signal when the time of next injection occurs.

The processor may have access to or may be configured to calculate a medical regimen associated with a user of the supplementary device. The medical regimen may comprise at least a series of times at which an injection operation is due to be performed. The processor may be configured to cause a reminder signal to be produced when a next injection operation is due, according to the medical regimen.

Producing an automatic reminder signals is advantageous for ensuring user compliance with their medical regimen, particularly where the user's medical regimen might mean there are many days between doses.

The supplementary device may further comprise a wireless unit for transmitting data to one or more external devices. The supplementary device may be further configured to send the reminder signal to the one or more external devices. For example, the stored information could be transmitted to the user's computer or smart phone wirelessly, for example over a Bluetooth connection.

The supplementary device may further comprise an optical sensor configured to read information visible on a housing of the injection device, the information identifying a medicament contained in the drug delivery device. This is advantageous as it allows the supplementary device to check the type and concentration of the medication in the drug delivery device before injection. The supplementary device may warn the user if the type or concentration of medication in the attached drug delivery device is incorrect.

The supplementary device may further comprise an outer needle cap sensor configured to output signals indicative of whether an outer needle cap is attached to the drug delivery device. The processor may be configured to receive the signals output from the outer needle cap sensor and to determine whether the outer needle cap is attached or not attached. If the processor determines that the drug delivery device is in a post-activation state and that the outer needle cap is not attached then, after a predetermined time, the processor may be configured to cause an alarm signal to be output. Causing an alarm signal to be output may comprise causing the supplementary device to emit one or more sounds and/or to display one or more indications on a display unit of the supplementary device.

This feature helps to avoid needle clogging which can occur if the drug delivery device is stored without the outer needle cap attached. The signal indicative of whether the outer needle cap is attached may also be sent to a user's smart phone or other portable device, so that they can be notified of the problem, even if they are not located near to the drug delivery device. The removal of the outer needle cap can also be used as a trigger. The removal of the outer needle cap may trigger the supplementary device to power on and to begin its monitoring processes. Therefore the user does not need to perform any additional operations to begin using the supplementary device. This greatly simplifies use of the supplementary device for a user. Similarly, the replacement of the outer needle cap may trigger the supplementary device to turn off, thus saving power.

The drug delivery device may be a powered auto-injector.

A second aspect provides a system comprising the supplementary device of the first aspect and the drug delivery device. The drug delivery device may be a powered auto-injector. A dispensing mechanism of the powered auto-injector may be powered by a pre-compressed spring.

Auto-injectors are devices that completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Forces required of the user/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

The correct administration of drugs and its termination is important for the safety and efficacy of the drug (pharmacovigilance). Failures in administration through the user can be minimized by monitoring of the injection device and the application time. Typical patient failures are:

1. The user may forget the correct day of maturity for their next injection. This is particularly the case for medication intervals longer than a day, e.g. twice a week, every, second day, bi-weekly, or therapy specific intervals such as 1st week twice, 2nd week every 2nd day, as of third week 2, 2, 3—interval, e.g.

2. The user may let too much time pass between removing the auto injector cap and performing the injection, resulting in needle clogging and/or device stalling.

3. The user does not carry out the holding time (also know as "dwell time") after the end of injection.

The disclosure describes a re-usable add-on device suitable for use with one shot auto-injectors and which may record the injection history, monitor the dose administration and aid the patient in performing the injection correctly and on time.

DETAILED DESCRIPTION

In the following, embodiments will be described with reference to an auto-injector. The present invention is however not limited to such application and may equally well be deployed with injection devices that eject other medicaments, or with other types of drug delivery devices, such as syringes, pre-filled syringes, needleless injectors and inhalers.

Figure 1A:
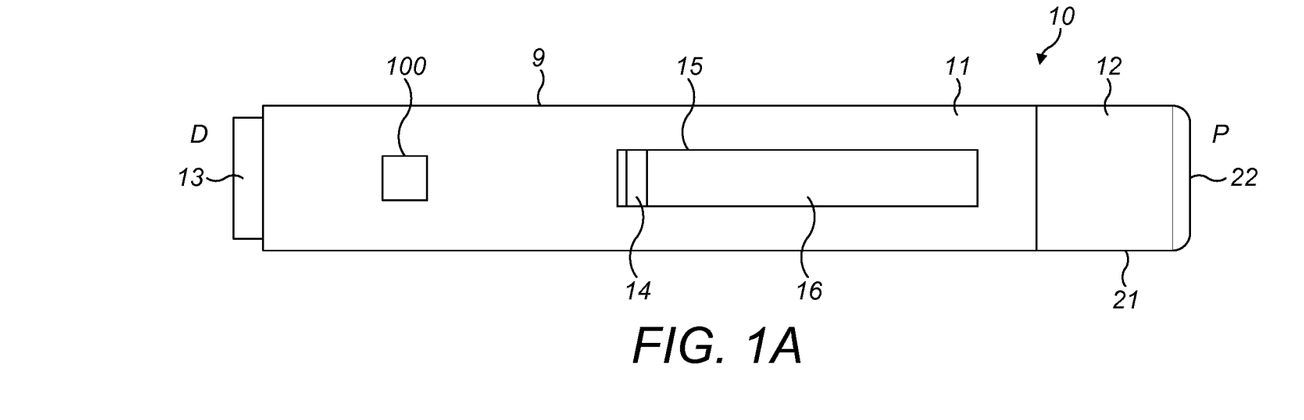
FIG. 1: an exploded view of an injection device.

An injection device 10 according to embodiments will now be described with reference to FIGS. 1A and 1B. In some embodiments, the injection device 10 is a single use auto-injector 10. The auto-injector 10 has a proximal end P and a distal end D. The proximal end P is directed towards the injection site of a patient during an injection while the distal end D is directed away from the injection site.

The auto-injector 10 comprises a body 9 and a cap 12 (also referred to herein as the outer needle cap or ONC 12). The body 9 comprises an outer housing 11. The outer housing 11 is an elongate tube. The outer housing 11 includes a cartridge holder or syringe holder (not shown) which supports a cartridge or syringe 18 containing liquid medicament 16. Hereafter the description shall refer to a cartridge 18, which is supported by a cartridge holder (not shown). The cartridge 18 is shown in broken lines in FIG. 1B.

The outer housing 11 also houses a dispense mechanism (not shown) for causing dispensing of the medicament 16 during injection.

A hollow needle 17 communicates with an interior volume of the cartridge 18 and serves as a conduit for liquid medicament 16 during injection. The needle 17 and the cartridge 18 are in a fixed position relative to each other and to the body 9. A stopper, plunger, piston or bung 14 is moveable within the cartridge 18 to as to expel medicament contained within the cartridge 18 through the needle 17 under action of the dispense mechanism.

The dispense mechanism is mechanically coupled to the piston 14 of cartridge 18. The dispense mechanism is configured to move the piston axially along the cartridge 18 in a proximal direction to dispense medicament 16 through the needle 17. The dispense mechanism includes components that cooperate to apply a force to the piston 14 in response to an actuation input provided by a user. Here, the actuation input that triggers application of a force to the piston 14 is received by way of a dose dispense button 13 that is located at the distal end of the auto-injector 10. The dispense mechanism is mechanically coupled to the dispense button 13.

The body 9 also comprises a cap support 19 at the proximal end of the outer housing 11. The cap support is concentric with the outer housing 11 and may have a smaller diameter. The cap support 19 extends from the proximal end of the housing 11. The ONC 12 is received over the cap support 19 to close the proximal end of the body 9 and to cover the needle 17. The ONC 12 comprises a cylindrical wall 21 and an end wall 22. With the ONC 12 located on the body 9, as shown in FIG. 1A, an internal surface of the cylindrical wall 21 abuts an external surface of the cap support 19 in tightly abutting relation so that the ONC 12 is retained thereon in an attached position.

Figure 1B:
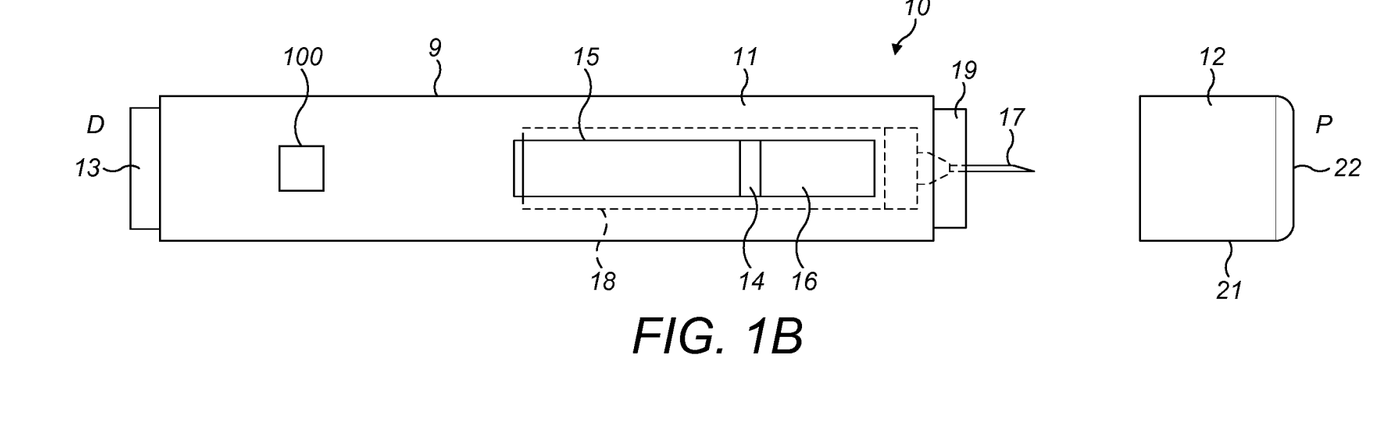

To inject the medicament 16, the ONC 12 is removed from the device 10 by the user, resulting in the arrangement shown in FIG. 1B. Next, the proximal end of the auto-injector 10 is placed against an injection site of a patient, which may be the user or another person. The user then actuates the dispense button 13. This causes the dispense mechanism to force the piston 14 to expel medicament from the cartridge 18 through the needle 17 into the injection site of the patient.

The cartridge 18 is transparent and a window 15 is provided in the housing 11 coincident with the cartridge 18 so that the medicament 16 contained within the cartridge 18 is visible. A user of the auto-injector thus is able by inspection to determine whether the entire quantity of medicament 16 has been ejected from the cartridge 18 during the injection.

A label is provided on the housing 11. The label includes information 100 about the medicament included within the injection device 10, including information identifying the medicament. The information 100 identifying the medicament may be in the form of text. The information 100 identifying the medicament may also be in the form of a color. The information 100 identifying the medicament may also be encoded into a barcode, QR code or the like. The information 100 identifying the medicament may also be in the form of a black and white pattern, a color pattern or shading.

Figure 2:
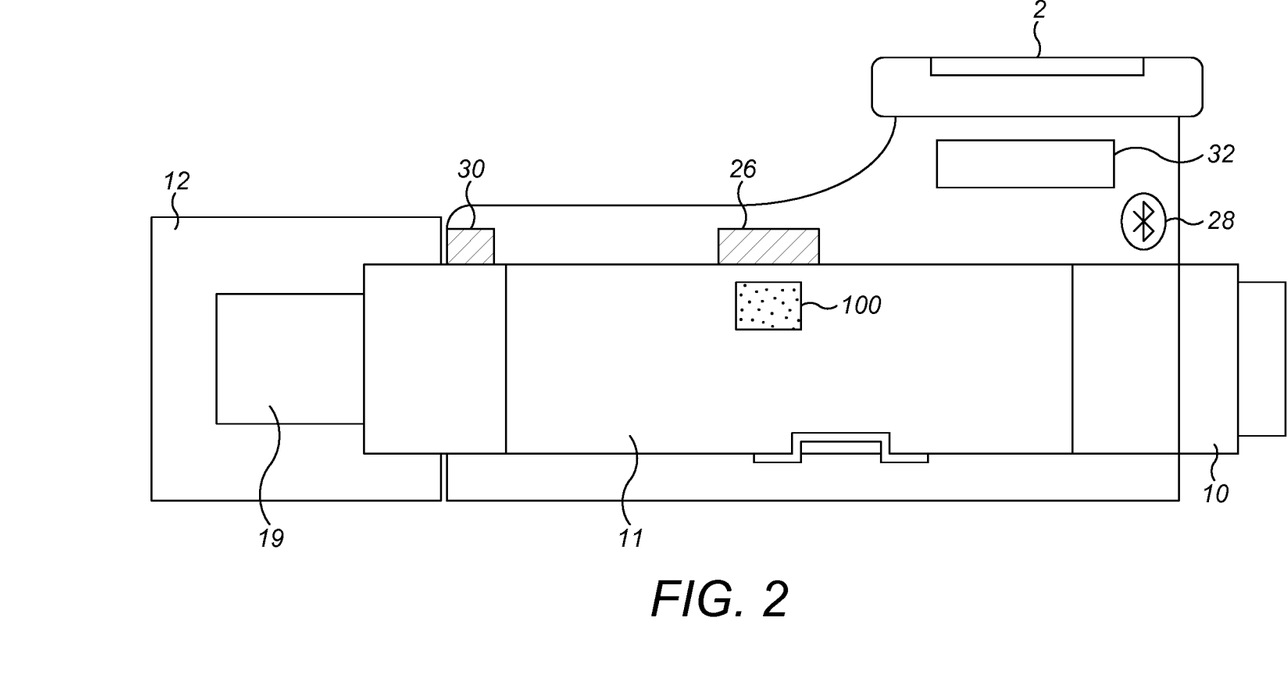
FIG. 2: a schematic illustration of a supplementary device releasably attached to the injection device of FIG. 1.

FIG. 2 is a schematic illustration of an embodiment of a supplementary device 2 to be releasably attached to injection device 10 of FIG. 1. Supplementary device 2 comprises a housing 20 configured to embrace the housing 11 of injection device 10 of FIG. 1, so that the injection device 10 is at least partially retained within the supplementary device 2, but is nevertheless removable from the supplementary device 2, for instance when injection device 10 is empty and has to be replaced. The injection device 10 and supplementary device 2 may comprise co-operating alignment features to ensure that the supplementary device 2 is correctly orientated and positioned with respect to the injection device 10. For example, the injection device 10 and supplementary device 2 may be releasably secured together using a bayonet fitting where the injection device 10 has a protrusion on the housing 11 and the supplementary device 2 has a corresponding groove for receiving the protrusion.

Information is displayed via display unit 21 of supplementary device 2. The display unit may be a touch sensitive screen. The supplementary device 2 may also comprise at least one hardware input (not shown) such as a push button. The supplementary device 2 has an outer needle cap (ONC) sensor 30. The ONC sensor may be any suitable form of proximity sensor, which allows the supplementary device 2 to determine whether the ONC 12 is attached to the injection device 10 or not. The supplementary device 2 also comprises an optical sensor 26 for reading the information 100 identifying the medicament. The information 100 identifying the medicament may be the color of the housing 11 of the injection device, or the color of an area of the housing or a label affixed to the housing. In these embodiments, the optical sensor 26 may be a simple photometer configured to detect the color. In some other embodiments, the information 100 identifying the medicament may be a QR code, or other similar encoded information and the optical sensor 26 may be a camera or QR reader.

The processor 24 may be configured to check the information 100 read by the optical sensor 26 against pre-stored information in order to verify that the user is injecting the correct medicament. If the processor 24 does not recognize the information 100 or recognizes the information 100 as indicating a different medicament to that which the user should be receiving at that time, then the supplementary device 2 may produce an alarm signal. The alarm signal may comprise words or graphics displayed on the display unit 21. Alternatively, or in addition, the supplementary device 2 may send an alarm signal to the external device.

The supplementary device 2 comprises a battery 32 to power the other components. The supplementary device 2 comprises a wireless communication module 28 for communicating information with an external device. In some embodiments, the wireless communication module 28 is a Bluetooth communication module 28.

Figure 3:
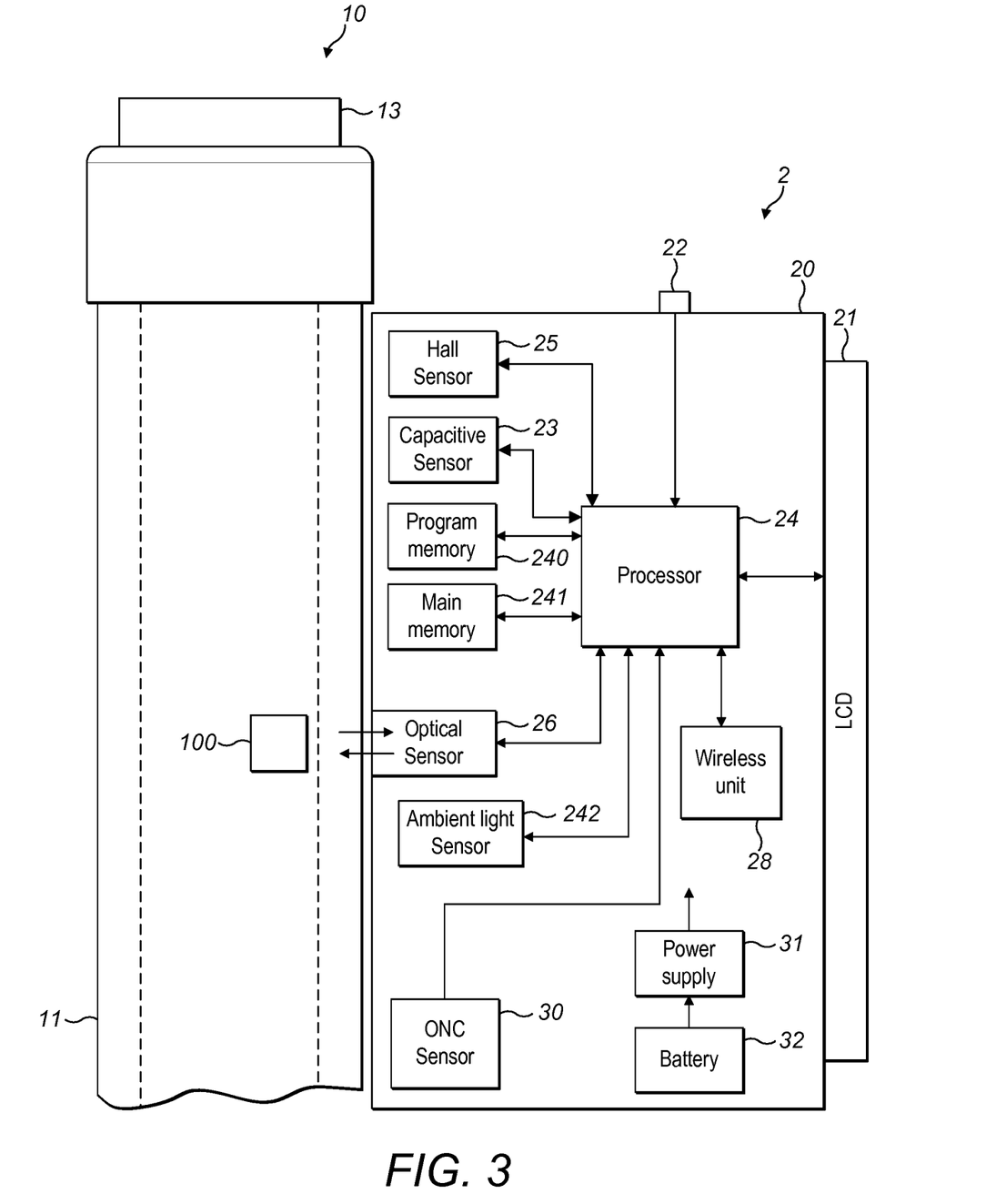
FIG. 3: a schematic view of a supplementary device attached to a injection device showing components of the supplementary device.

FIG. 3 shows a schematic view of the supplementary device 2 of FIG. 2 in a state where it is attached to injection device 10 of FIG. 1.

A plurality of components are contained within the housing 20 of supplementary device 2. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

Supplementary device 2 may optionally further comprises at least one input transducer, illustrated schematically as a button 22. These input transducer 22 allows a user to turn on/off supplementary device 2, to trigger actions (for instance to cause establishment of a connection to or a pairing with another device, and/or to trigger transmission of information from supplementary device 2 to another device), or to confirm something. In some other embodiments, the supplementary device 2 is automatically turned on/off via the ONC sensor 30.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls a Capacitive Sensor 23 and/or a Hall Sensor 25. In some embodiments, the supplementary device 2 comprises only the capacitive sensor 23 while in some other embodiments the supplementary device 2 comprises only the Hall sensor 25. In some further embodiments, the supplementary device 2 comprises both the capacitive sensor 23 and the hall sensor 25 where one may act as a redundant/back-up system for the other. These sensors 23, 25 are configured to output signals indicative of the positions of one or more components within the injection device 10. These sensors 23, 25 may collectively be referred to as non-contact sensors, since they are able to sense the absolute position and movement of components within the attached injection device 10 without contact between the sensors 23, 25 and any of the components sensed. The processor 24 receives these signals, infers an operational state of the injection device 10, and causes information regarding the timing of the operation of the injection device 10 to be recorded in the main memory 241 and/or transmitted to an external device via the wireless unit 28. The operation of these sensors is described in greater detail with respect to FIGS. 4 and 5.

Processor 24 further controls an optical sensor 26, that is configured to determine an optical property of the housing 11 of injection device 1, for example a color or a shading or a more complex pattern, such as a QR code. The optical property may only be present in a specific portion of housing 11, for example on a label affixed to the housing 11. Information on the color/pattern is then provided to processor 24, which may then determine the type of injection device 10 and/or the type of medicament contained in injection device 10. The optical sensor 26 may be a camera unit, and an image of the housing 11 may then be provided to processor 24 to determine the color of the housing, sleeve or medicament container by way of image processing. Further, one or more light sources may be provided to improve reading of optical sensor 26. The light source may provide light of a certain wavelength or spectrum to improve color detection by optical sensor 26. The light source may be arranged in such a way that unwanted reflections, for example due to the curvature of the housing 11, are avoided or reduced. In an example embodiment, the optical sensor 26 is a camera unit configured to detect a code 100 (for instance a bar code, which may for instance be a one- or two-dimensional bar code) related to the injection device and/or the medicament contained therein. This code 100 may for instance be located on the housing 11 or on a medicament container contained in injection device 10, to name but a few examples. This code 100 may for instance indicate a type of the injection device and/or the medicament, and/or further properties (for instance an expiration date). This code 100 may be a QR code 100. The QR code is in general black and white and thus no color detection is required on the part of the optical sensor 26. This allows the optical sensor 26 to be simple and cheap to manufacture.

Processor 24 controls a wireless unit 28, which is configured to transmit and/or receive information to/from another device in a wireless fashion. Such transmission may be based on radtransmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fiber connection. When data is transmitted, the units of the data (values) transferred may be explicitly or implicitly defined. For instance, in case of an insulin dose, always International Units (IU) may be used, or otherwise, the used unit may be transferred explicitly, for instance in coded form. The transmitted data may also include a time stamp associated with an injection.

Processor 24 receives an input from an ONC sensor 30, which is operable to detect whether the outer needle cap 12 is present, i.e. to detect whether the outer needle cap 12 is coupled to the injection device 1. A battery 32 powers the processor 24 and other components by way of a power supply 31. The removal of the ONC 12 is detected by the ONC sensor 30 and can be used as a wake-up or switch on trigger. Thus, the supplementary device may automatically turn on and begin its monitoring processes when the ONC 12 is removed. Similarly, when the ONC 12 is replaced the supplementary device may automatically power off, thus saving battery power.

The supplementary device 2 of FIG. 3 is thus capable of determining information related to a condition and/or use of injection device 1. This information is displayed on the display 21 for use by the user of the device. The information may be processed by supplementary device 2 itself, or may be at least partially provided to another device (e.g. a blood glucose monitoring system or a computing device).

The processor 24 is configured to receive signals form the ONC sensor 30 and to detect when the ONC 12 is not attached to the injection device 10. If the user stores the injection device 10 without the ONC 12 attached, then the needle 17 can become clogged. Therefore, the supplementary device 2 is configured to produce an alarm signal if the processor 24 detects that the ONC 12 has been un-attached for a predetermined length of time following an injection operation. The alarm signal may be sent via the wireless unit 28 to the external user device such that the user can be alerted to the need to replace the ONC 12 even if they have moved away from the supplementary device 2 and injection device 10. Alternatively, or in addition, the alarm signal may comprise the supplementary device 2 displaying words and/or graphics on the display unit 21 or producing sound.

Figure 4A:
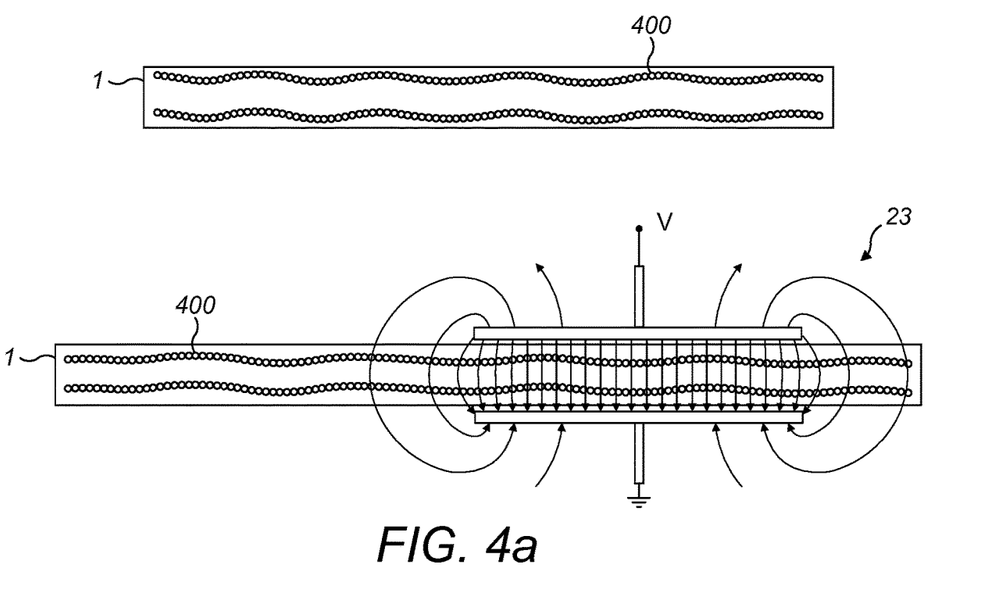
FIG. 4a: a schematic illustration of an injection device and sensor components of the supplementary device for capacitive sensing of the status of the injection device.
Figure 4B:
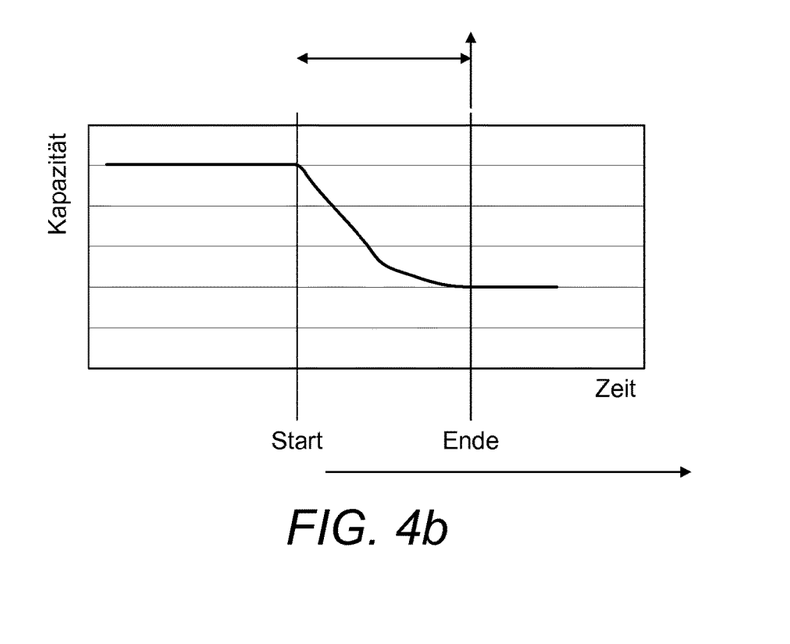
FIG. 4b: a graph illustrating the response of the sensor components shown in FIG. 4a during an injection procedure of the injection device.

In some embodiments, the supplementary device 2 comprises a capacitive sensor 23. Referring now to FIGS. 4a and 4b, the operation of the capacitive sensor 23 will be described in greater detail.

FIG. 4a illustrates shows diagrammatically a cut-away through the injection device 10 when the injection device is in a pre-injection configuration and a post injection configuration (also referred to as pre-activation and post-activation). The injection device 10 comprises a drive spring 400, which is pre-compressed during assembly of the injection device 1. The drive spring 400 is maintained in this pre-compressed state until an injection is performed. When a user triggers an injection operation by pressing dose dispense button 13, the dispense mechanism is released and the drive spring decompresses so as to dispense medicament from the cartridge 18.

Various components of the capacitive sensor 23 are shown schematically in the lower image in FIG. 4a. The capacitive sensor 23 comprises opposing sets of at least one electrically conductive plate. The plates are supported in the housing 20 of the supplementary device 2 so as to be adjacent to the injection device 10 when the supplementary device 2 is attached. The plates may be curved to better fit the contours of the supplementary device housing 20. The plates are connected in a circuit so as to form a capacitor. The injection device 10 occupies the space between the plates and functions as the dielectric layer of the capacitor. The capacitive sensor 23 sends signals to the processor 24 via which the processor 24 can determine the effective capacitance. For example, the processor 24 may control the application of charge to one plate of the capacitive sensor 23 and then measure the time taken for the capacitive sensor 23 to discharge.

The upper image in FIG. 4a shows the approximate position of the drive spring 400 before an injection has been performed. The drive spring 400 is compressed, with the coils of the spring being closely spaced or touching. The lower image in FIG. 4a shows the approximate position of the drive spring 400 after the energy stored therein has been released during an injection process. The coils of the drive spring are spaced further apart. In some embodiments, the drive spring is metallic.

FIG. 4b is a graph showing an exemplary relationship between capacitance and charge before, during and after an injection process. Before the injection deice 1 is used, the capacitance measured by the capacitive sensor 23 is relatively high, due to the presence of a greater amount of the drive spring 400 in the region between the capacitor plates. The start and end points of the medicament ejection process are shown. During the ejection, the drive spring 400 uncoils such that progressively less of its material is disposed in the region between the capacitor plates. Therefore, the capacitance measured by the capacitive sensor 23 decreases during the ejection. After the injection device 10 has been used, the capacitance measured by the capacitive sensor 23 is relatively low.

The processor 24 may be configured to determine that an injection has been completed if the capacitance drops from the relatively high value to the relatively low value and remains there for a predetermined time. The processor 24 may be configured to detect the gradual change in measured capacitance in order that the supplementary device 2 can distinguish between an injection process and the supplementary device 2 being removed from the injection device without an injection being performed, in which case a more sudden drop in capacitance would be expected. The capacitive sensor 23 may be shielded so as to protect it from external electromagnetic impulses.

Figure 5A:
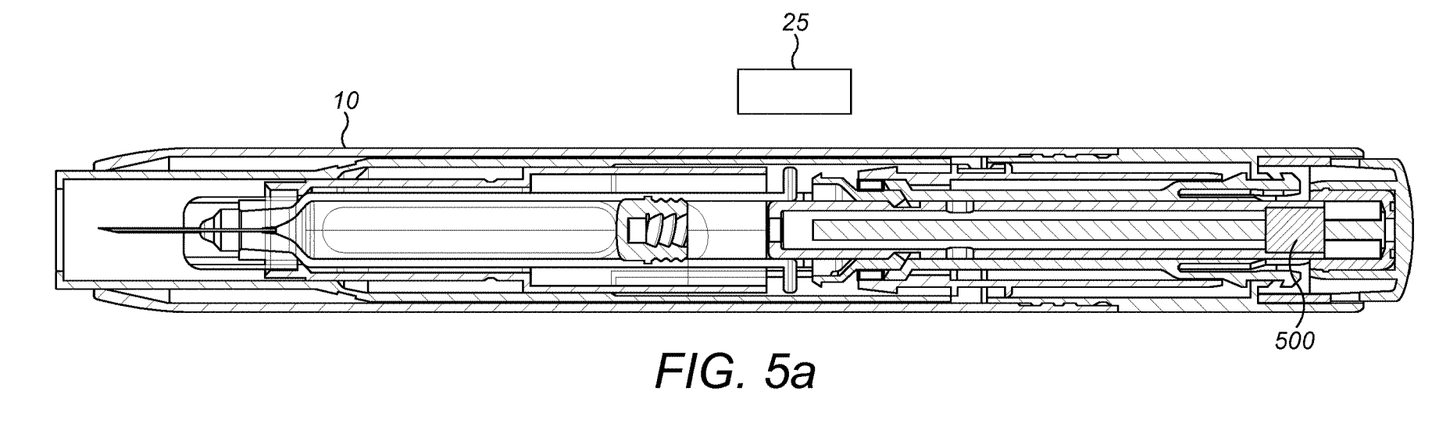
FIGS. 5a and 5b: cutaway illustrations of an injection device showing the possible position of internal magnets and sensors for use in sensing of the status of the injection device.
Figure 5B:
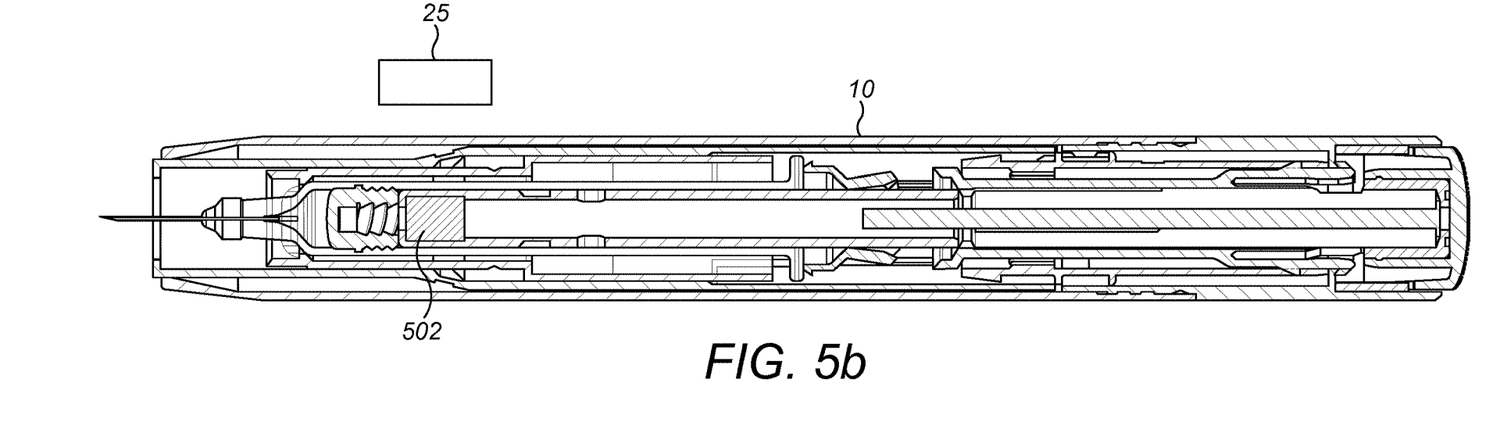

In some embodiments, the supplementary device 2 comprises a Hall sensor 25 (also referred to as a Hall Effect sensor or magnetic sensor). Referring now to FIGS. 5a and 5b, the operation of the Hall sensor 25 will be described in greater detail. In these embodiments, a magnet 500 is mounted within the injection device 10 on either the distal or the proximal end of the plunger. FIG. 5a illustrates an embodiment in which the magnet 500 is mounted on the distal end of the plunger. The injection device 10 of FIG. 5a is in a pre-activation state. The Hall sensor 25 is positioned within the supplementary device 2 such that it overlays the approximate midpoint of the injection device 10 when the two devices are connected together. This is approximately the longitudinal position that the magnet 500 will occupy at the end of the injection process.

In the pre-activation state, the Hall sensor 25 will detect a very low or no magnetic field due to the relatively large separation between the magnet 500 and Hall sensor 25. During the ejection process, the field detected by the Hall sensor 25 increases. When the injection device 10 is in a post-ejection state, the magnet is located adjacent the Hall sensor 25 and the field detected is relatively high.

FIG. 5b illustrates an alternative arrangement in which a magnet 502 is supported on the proximal end of the plunger. The injection device 10 of FIG. 5b is in a post-activation state. The Hall sensor 25 is positioned further towards the proximal end of the supplementary device 2. The choice of whether to use the design in FIG. 5a, or that of FIG. 5b may depend on the size of the supplementary device 2 and its position when mounted to the injection device 10 or on the construction process of the injection device 10.

As with the embodiment described above with reference to FIGS. 4a and 4b, the processor 24 receives the signals from the Hall sensor 25 and can determine whether the injection device 10 is in a pre-injection or post-injection state.

The magnet 500, 502 may be a permanent magnet or alternatively a Ferro magnetic plastic. An advantage of using a plastic magnet is that it can be molded to the plunger rod during manufacturing. The plastic magnet may need to be magnetized shortly before final assembly of the injection device 10 using a magnetic pulse field.

The processor 24 is configured to receive signals from the capacitive sensor 23 and/or Hall sensor 25 and to infer whether the injection device 10 is in a pre-injection state, a post-injection state or whether an injection process is ongoing. The processor 24 may control the display unit 21 to display different indications to a user depending on the state of the device. This is advantageous as some users may find it difficult to tell whether an injection device 10 has been used or not, and as it aids with the injection operations itself, which some users may find difficult without the presence of the supplementary device 2.

Figure 6A:
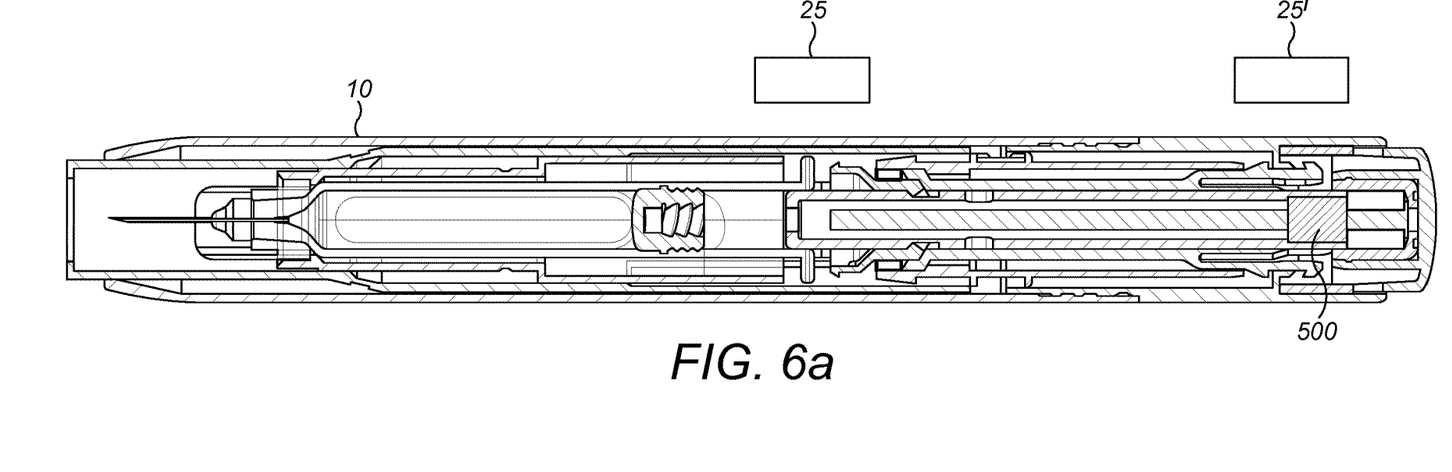
FIGS. 6a, 6b and 7: further cutaway illustrations of an injection device showing the possible position of internal magnets and sensors in three alternative embodiments.
Figure 6B:
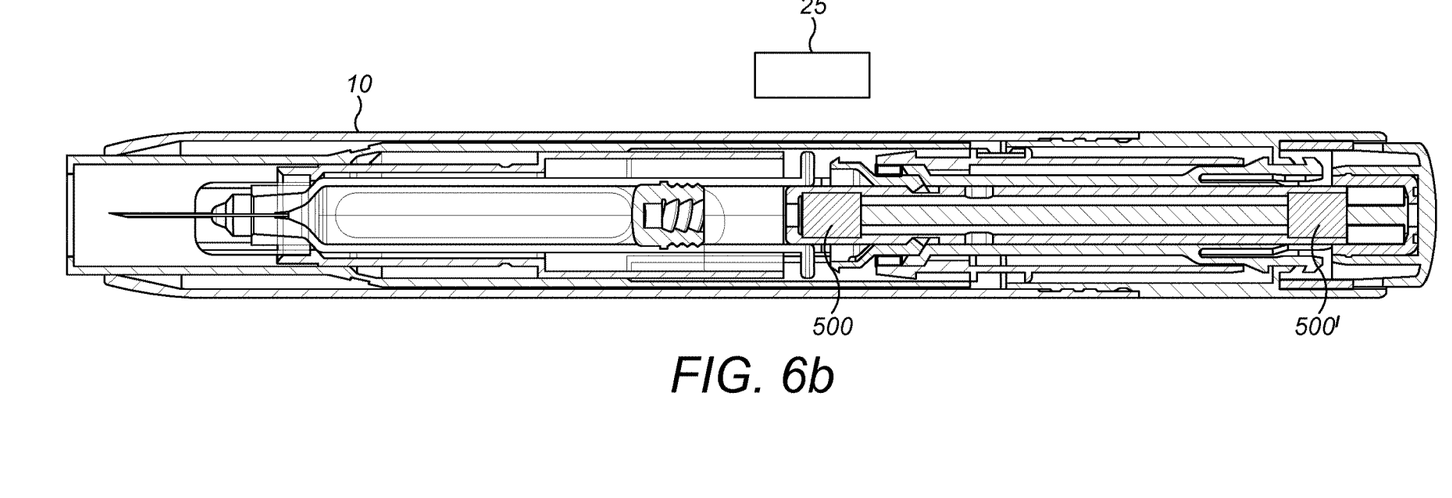

FIGS. 6a and 6b show alternative embodiments in which one or more Hall sensors are used. Both figures show the injection device 10 in a pre-activation state. In FIG. 6a, the supplementary device 2 comprises a first Hall sensor 25 and a second Hall sensor 25'. The first and second Hall sensors are arranged in the supplementary device 2 so as to be spaced at different longitudinal positions along the injection device 10. For example, the first Hall sensor 25 may be positioned in the supplementary device 2 so as to be located over the center region of the injection device 10, while the second Hall sensor 25' may be positioned so as to be located close to the distal end of the injection device 10. The injection device 10 comprises a magnet 500 mounted to the distal end of the plunger. As the magnet 500 moves past the first and second Hall sensors 25, 25', signals are induced in the sensors, which can be used to determine the position of the plunger.

When the injection device 10 is activated, the magnet 500 first moves past the second Hall sensor 25'. Signals induced in the second Hall sensor 25' are received by the processor 24 and are used to determine that the plunger has begun its movement. Thus, the processor 24 is able to determine that an ejection process has begun. As the magnet 500 moves away from the second Hall sensor 25', the signal produced diminishes. As the magnet 500 approaches the first Hall sensor 25, the signal from this sensor increases. As the plunger reaches its final position, the magnet 500 passes underneath the first Hall sensor 25. The first Hall sensor 25 may be positioned such that the magnet 500 stops underneath the sensor 25 or moves completely past the sensor. In either case, the processor 24 is configured to determine, from the received signals, that the plunger has successfully reached its final position.

In FIG. 6b, the supplementary device 2 comprises a single Hall sensor 25. The injection device 10 comprises a first magnet 500 mounted to the proximal end of the plunger and a second magnet 500' mounted to the distal end of the plunger. The Hall sensor 25 is positioned so that it is located over the central region of the injection device 10 and so that the first magnet 500 is located underneath or near the sensor 25. When the injection device 10 is activated, the first magnet 500 moves underneath and away from the Hall sensor 25. Signals induced in the Hall sensor 25 are received by the processor 24 and are used to determine that the plunger has begun its movement. Thus, the processor 24 is able to determine that an ejection process has begun. As the plunger reaches its final position, the second magnet 500' passes underneath the Hall sensor 25. The Hall sensor 25 may be positioned such that the second magnet 500' stops underneath the sensor 25 or moves completely past the sensor. In either case, the processor 24 is configured to determine from the received signals that the plunger has successfully reached its final position.

In the arrangements shown in FIGS. 5a and 5b, the processor can only determine when the plunger arrives at its final position. In the arrangements of FIGS. 6a and 6b, the processor 24 can determine both that the ejection process has successfully begun and that it has completely finished. Having both these determinations allows for better malfunction detection and reporting. This is advantageous, as the injection device 10 itself has no means for detecting malfunctions. Some injection devices have a mechanically operated inspection window, which turns from red to green during injection, but the remote sensing and detection abilities of the supplementary device 2 provide much more useful information and more accurate and reliable detection of malfunctions.

For example, the processor can determine that the plunger has begun its movement and has continued to move away from its initial position. If, when the injection device 10 is activated, this detection is not made, the processor 24 can determine that the plunger has not moved and that no (or little) medicament has been ejected. If the processor 24 detects that the plunger has begun its movement but does not detect that it has reached its final position, it can be determined that some medicament has been ejected, but not the whole amount. The processor 24 is configured to write information regarding operation of the device and also details of any malfunctions into the log of the supplementary device 2. This can then be reviewed and evaluated, either by the user or the user's health care professional. Being able to determine not only that a malfunction has occurred, but also whether any medicament has been ejected or not, is potentially important information, as it will likely inform how to proceed with the user's therapy. Informing a user that there has been a device malfunction but that some medicament has been injected helps to prevent accidental overdosing. The supplementary device 2 can additionally sound an alarm and present information to the user via display unit 21. For example, the user can be instructed to seek the advice of their doctor, due to a malfunction of the injection device 10 and can also be informed as to whether any medicament has been ejected from the device.

In some embodiments, the supplementary device 2 comprises either the capacitive sensor 23 or the Hall sensor 25, however in some other embodiments, both sensors may be provided in different parts of the supplementary device 2.

Figure 7:
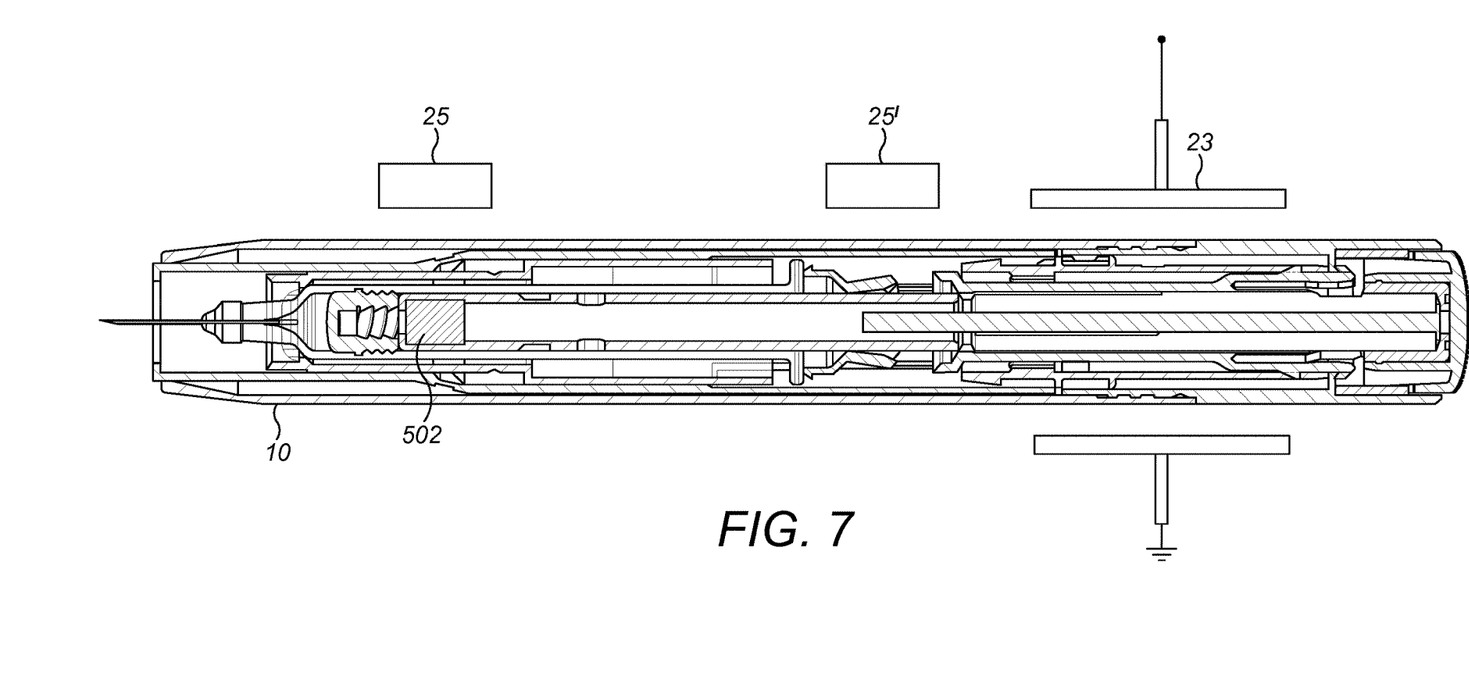

In embodiments where the supplementary device comprises both the capacitive sensor and the Hall sensor, the signals from both of these may be used to detect any mechanical failure of the drug delivery device. FIG. 7 shows an embodiment of the supplementary device 2 comprising both the capacitive sensor 23 and first and second Hall sensors 25, 25'. FIG. 7 illustrates the injection device 10 in a post-activation state. The injection device 10 comprises a magnet 500 disposed on the proximal end of the plunger. As described above with reference to FIG. 6a, the magnet 500 begins underneath or near the second Hall sensor 25' and after activation of the injection device 10 moves away and towards the first Hall sensor 25. When the plunger reaches its final position, the magnet 500 is underneath or near the first Hall sensor 25. The capacitive sensor 23 may be provided at a different location in the supplementary device 2, as shown in FIG. 7. The capacitive sensor 23 is configured to operate as described above with reference to FIGS. 4a and 4b. In this arrangement, the magnet 500 is kept away from the capacitive sensor 23 so as not to affect its readings. Alternatively, the capacitive sensor 23 may be positioned between the two Hall sensors 25, 25' and software may be used to distinguish the signals due to the un-compressing of the spring 400 and the movement of the magnet 500.

Having both the capacitive sensor 23 and the Hall sensor 25, 25' allows further details on the type of any malfunction to be determined. For example, if the capacitive sensor 23 detects that the drive spring 400 has un-compressed, but the Hall sensors 25, 25' detect that the plunger has not moved, it can be inferred that a mechanical failure relating to the connection between the drive spring and plunger has occurred, either during manufacture or during use. If the Hall sensors 25, 25' detect that the plunger has moved or is not in the correct initial position, but the capacitive sensor 23 detects that the drive spring 400 in still completely compressed, it can be inferred that a mechanical fault has occurred, such as the injection device 10 was incorrectly assembled or does not contain the correct amount of medicament. Suitable alarm signals and information may be generated and displayed by the supplementary device 2 in response to these determinations. The system of FIG. 7 is also able to detect whether medicament has been ejected or not and so prevent accidental overdoses and inform on how to proceed with the user's therapy in the event of a malfunction.

The processor 24 is configured to record a user's injection history. While the injection device 10 may be a single use auto-injector, the supplementary device 2 is reusable, and is configured to be removed from a used injector 10 and attached to a new injector. The processor 24 of the supplementary device 2 has an internal clock in order to create time stamps associated with the injection events. The clock may be a relative clock or an absolute clock. The supplementary device 2 is configured to communicate with an external device through wireless unit 28 and the external device may provide an absolute time.

When the supplementary device 2 is first attached to a new injection device 10, the optical sensor 26 may be activated and the information 100 read. The supplementary device 2 may communicate the information to a user using the display screen 21. When a user performs an injection, this is detected by the capacitive sensor 23 or Hall sensor 25 as described above. A time stamp associated with the injection is then created by the processor 24. The processor 24 also records and associates with the time stamp the type of medicament injected, using the previously read information 100. An external device (not shown) in the user's possession may be registered and associated with the supplementary device 2. The external device may be a mobile computer or smart phone via the wireless unit 28. The mobile computer or smart phone may run a computer program for managing the user's medical records and injection history. The supplementary device 2 is configured to communicate the recorded injection information to the external device.

The processor 24 may be pre-programmed with information relating to the frequency at which the user should perform injections. This programming may take the form of a maximum time between injections or a medical regimen associated with the user of the supplementary device 2. For example, the processor 24 may be pre-programmed with information specifying that the maximum time between injections should be 24 hours. In some other embodiments, the medical regimen may be more detailed, such as to specify specific times of day at which the user is to perform an injection operation using the injection device 10. Alternatively, the processor 24 may be configured to calculate a time at which the user should next perform an injection based on the injection history. For example, the time at which the user should perform the next injection may depend on the amount of medicament previously injected and the frequency of the previous injections. The processor may use the previous injection history to calculate a medical regimen for the user.

When the processor 24 determines that it is time for the user to perform a subsequent injection, it causes a reminder signal to be sent via the wireless unit 28 to the associated external device. The external device may then notify and remind the user that their next injection is due. This is advantageous as the user may not wish to carry the injection device 10 and/or supplementary device 2 with them, but may in any case by carrying a smart phone or similar device. Thus, the user can be reminded of the need for a subsequent injection via a separate device which they carry with them. Furthermore, the injection device 10 may need to be kept under specific conditions, such as in a refrigerator or a freezer, thus, it is not possible for a user to carry the injection device with them. It is therefore easy for a user to forget about the times at which an injections needs to be performed.

In addition, the processor 24 may be configured to use signals received from the capacitive sensor 23 or Hall sensor 25 to instruct or inform a user regarding 'dwell time'. After a user injects a quantity of medicament into their skin, it is advantageous for the needle to be left in position for a short time (e.g. 5-20 seconds). This allows the medicament to be diffused away from the injection site by action of the user's blood flow. If the needle is removed too soon after an injection, it can result in medicament being expressed from the injection site and the user therefore not receiving a full dose. As previously stated the processor 24 can use the change in signals received from the sensors 23, 25 to determine that an injection is being performed. The processor 24 can infer, when the signals received from the sensors 23, 25 stop changing, that the injection has been completed. This detection can therefore be used as a trigger to display an indication to the user on the display unit 21 instructing them to leave the needle of the injection device 10 in the injection site for a predetermined length of time. The indication may be of any suitable form, for example a timer, which counts up or down, or a graphic which gets larger/smaller or which fills or un-fills. Other methods of indication may also be used, such as sound.

In addition to the components described above, the supplementary device 2 may comprise an ambient light sensor 242. Sometimes the injection device 10 may need to be stored in a refrigerator or a freezer in order to prevent degradation of the medicament over a period of time. The user may attach the supplementary device 2 to an unused injection device 10 after a previous injection, and store the resulting combined system in the fridge/freezer. The ambient light sensor 242 of the supplementary device 2 can be used to detect when the fridge/freezer is opened. This can be used as a trigger for initiating an alarm to remind the user regarding the due time of their next injection. As described above this alarm may take the form of sound emitted by the supplementary device 2, text/graphics displayed on the display unit 21, and/or a reminder send via the wireless unit 28 to the user's smart phone or other external device.

The invention claimed is:

1. A supplementary device configured to be attached to a drug delivery device, the supplementary device comprising:
a non-contact sensor configured to output signals indicative of a position of a moveable component within the drug delivery device, and
a processor configured to receive the output signals from the non-contact sensor and to determine based on the output signals whether the drug delivery device is in a pre-activation state or a post-activation state,
wherein the non-contact sensor is a Hall sensor configured to measure a magnetic field produced by the moveable component within the drug delivery device; and
wherein the supplementary device further comprises a capacitive sensor and wherein components of the capacitive sensor are arranged within the supplementary device such that when the drug delivery device is attached to the supplementary device, the drug delivery device forms at least a part of a dielectric layer of the capacitive sensor.

2. The supplementary device according to claim 1, wherein the supplementary device comprises an additional Hall sensor configured to measure a magnetic field produced by the moveable component within the drug delivery device and wherein the Hall sensor and the additional Hall sensor are separated from each other in a direction of movement of the moveable component.

3. The supplementary device according to claim 1, wherein the supplementary device further comprises an optical sensor configured to read information visible on a housing of the drug delivery device, the information identifying a medicament contained in the drug delivery device.

4. The supplementary device according to claim 1, wherein the drug delivery device is a powered auto-injector.

5. The supplementary device according to claim 1, wherein upon determining that the drug delivery device has changed from the pre-activation state to the post-activation state, the processor is configured to cause an indication to be outputted which informs a user regarding a dwell time of the drug delivery device.

6. The supplementary device according to claim 5, wherein the supplementary device further comprises a display unit and wherein causing the indication to be outputted comprises causing at least one graphical elements to be displayed on the display unit, the at least one graphical elements communicating a progress of the dwell time.

7. The supplementary device according to claim 1, wherein the supplementary device further comprises at least one memory and wherein the processor is configured to cause information relating to a last performed injection operation to be stored in the memory upon determining that the drug delivery device has changed from the pre-activation state to the post-activation state, wherein the information comprises at least a time stamp associated with the last performed injection operation.

8. The supplementary device according to claim 7, wherein the information further comprises a medicament dose amount and a medicament type.

9. The supplementary device according to claim 1, wherein the processor has access to or is configured to calculate a time of next injection and is further configured to produce a reminder signal when the time of next injection occurs.

10. The supplementary device according to claim 9, wherein the processor has access to or is configured to calculate a medical regimen associated with a user of the supplementary device, the medical regimen comprising at least a series of times at which an injection operation is due to be performed and wherein the processor is configured to cause the reminder signal to be produced when the injection operation is due according to the medical regimen.

11. The supplementary device according to claim 9, wherein the supplementary device further comprises a wireless unit for transmitting data to at least one external devices and wherein the supplementary device is further configured to send the reminder signal to the at least one external devices.

12. The supplementary device according to claim 1, wherein the supplementary device further comprises an outer needle cap sensor configured to output signals indicative of whether an outer needle cap is attached to the drug delivery device and wherein the processor is configured to receive the output signals from the outer needle cap sensor and to determine whether the outer needle cap is attached or not attached.

13. The supplementary device according to claim 12, wherein if the processor determines that the drug delivery device is in the post-activation state and that the outer needle cap is not attached then, after a predetermined time, the processor is configured to cause an alarm signal to be outputted.

14. The supplementary device according to claim 13, wherein causing the alarm signal to be outputted comprises causing the supplementary device to emit at least one sounds and/or to display at least one indications on a display unit of the supplementary device.

* * * * *